United States Patent
Ottiger et al.

(10) Patent No.: US 9,284,243 B2
(45) Date of Patent: Mar. 15, 2016

(54) PROCESS FOR THE PRODUCTION OF METHYLBUTYNOL

(71) Applicant: Lonza Ltd., Visp (CH)

(72) Inventors: Stefan Ottiger, Brig (CH); Thomas Scholl, Frauenfeld (CH); Stefan Stoffel, Unterbäch (CH); Klaus Kalbermatter, Brig-Glis (CH); Andreas Klein, Brig-Glis (CH); Kishore Nedungadi, Glis (CH)

(73) Assignee: LONZA LTD, Visp (CH)

( * ) Notice: Subject to any disclaimer, the term of this patent is extended or adjusted under 35 U.S.C. 154(b) by 0 days.

(21) Appl. No.: 14/407,144

(22) PCT Filed: Jul. 11, 2013

(86) PCT No.: PCT/EP2013/064651
§ 371 (c)(1),
(2) Date: Dec. 11, 2014

(87) PCT Pub. No.: WO2014/009452
PCT Pub. Date: Jan. 16, 2014

(65) Prior Publication Data
US 2015/0141709 A1    May 21, 2015

(30) Foreign Application Priority Data

Jul. 11, 2012   (EP) .................................. 12175996

(51) Int. Cl.
| | | |
|---|---|---|
| *C07C 29/42* | (2006.01) | |
| *C07C 29/76* | (2006.01) | |
| *C07C 29/80* | (2006.01) | |
| *B01D 61/36* | (2006.01) | |

(52) U.S. Cl.
CPC .............. *C07C 29/76* (2013.01); *B01D 61/362* (2013.01); *C07C 29/42* (2013.01); *C07C 29/80* (2013.01); *B01D 2311/2669* (2013.01)

(58) Field of Classification Search
CPC ...................................................... C07C 29/42
USPC .......................................... 568/873, 874, 878
See application file for complete search history.

(56) References Cited

U.S. PATENT DOCUMENTS

| | | | | |
|---|---|---|---|---|
| 3,301,771 A | * | 1/1967 | Vittorio Cariati et al. ....... 203/69 |
| 3,755,469 A | * | 8/1973 | Pasedach et al. ............. 568/597 |
| 6,147,266 A | * | 11/2000 | Lee et al. ...................... 568/874 |

FOREIGN PATENT DOCUMENTS

| | | |
|---|---|---|
| DE | 1193496 | 5/1965 |
| DE | 102005037430 A1 | 11/2011 |
| EP | 0610775 A1 | 8/1994 |
| GB | 1023856 A | 3/1966 |

OTHER PUBLICATIONS

Alzate, F; "Design and performance of two-phase flow pervaporation and hybrid distillation process," Eindhoven, Netherlands, 2006.
Tusel, et al, "Use of Pervaporation Systems in the Chemical Industry," Desalination, vol. 53., 1994.
Glinos, et al, "Design of Sidestream Distillation Columns," Ind. Eng. Chem. Process Des. Dev., vol. 24, pp. 822-828, 1985.
Ulrich, et al, "Influence of Impurities on the Control of Heterogeneous Azeotropic Distillation Columns," Ind. Eng. Chem. Process Des. vol. 41, pp. 230-250, 2002.
Waldburger, et al, "Kombination von Veresterung and Pervaporation in einem kontinuierlichen Membranreaktor—Combination of Esterification and Pervaporation in a Continuous Membrane Reactor," Chem. Ing.-Tech., vol. 66, pp. 850-854, VCH Weinheim, DE.

* cited by examiner

*Primary Examiner* — Sikarl Witherspoon
(74) *Attorney, Agent, or Firm* — Hoffman & Baron, LLP

(57) ABSTRACT

Subject of the invention is a process for the production of methylbutynol, wherein the process comprises at least one pervaporation step. In a preferred embodiment, the process comprises the steps of
(a) providing a feed composition comprising methylbutynol and water,
(b) subjecting the feed composition to distillation in a distillation device,
(c) removing a sidestream from the distillation device, the sidestream having a higher water content than the feed composition, and
(d) subjecting said sidestream to pervaporation, thereby reducing the water content.

The invention also relates to uses and devices relating to the inventive process.

14 Claims, 2 Drawing Sheets

PROCESS FOR THE PRODUCTION OF METHYLBUTYNOL

FIELD OF THE INVENTION

The invention relates to a process for the production of methylbutynol, wherein the process comprises at least one pervaporation step. The invention also relates to uses and devices relating to the inventive process.

BACKGROUND OF THE INVENTION

Methylbutynol (2-methyl-3-butyn-2-ol; $C_5H_8O$; CAS-Nr. 115-19-5), is an important intermediate in organic synthesis. For example, it is used in the production of isoprene, vitamins A and E, various pharmaceuticals and aroma compounds. On an industrial scale, methylbutynol is usually produced by reacting acetone with acetylene. Thereby, a crude reaction product is obtained, which comprises significant amounts of water and unreacted acetone. The reaction is carried out in the presence of catalysts and in specific solvents, such as liquid ammonia, acetals or ethers, which are also components of the crude reaction product. Further, salts and low-boiling organic by-products may be present in the crude reaction product.

In order to obtain pure methylbutynol it is necessary to remove water, acetone and further ingredients from the crude reaction product. However, removal of water is difficult because the boiling point of water is in the same range as the boiling point of methylbutynol (104° C.). Further, water and methylbutynol form an azeotrope boiling at about 91° C., consisting of about 70.5 to 72.5% (w/w) methylbutynol and 27.5 to 29.5% (w/w) water. Thus, water removal by normal distillation is not possible.

Acetone, which may be present in the crude reaction product in amounts of about 0.5 to 10% (w/w), has a boiling point of 56° C. and is removable by distillation. However, important reactions, such as polymerization of isoprene with Ziegler catalysts, are inhibited by trace amounts of acetone. Therefore, for many applications of methylbutynol it is necessary to remove acetone from the methylbutynol almost quantitatively, for example to a level below 0.03% (w/w).

According to prior art, the crude reaction product of the reaction of acetone and acetylene comprising the desired methylbutynol is usually subjected to azeotropic distillation in the presence of an entrainer forming an azeotrope with water. The entrainer/water azeotrope is removed from the reaction mixture by distillation. Low-boiling acetone is also removed with the distillate while methylbutynol containing low residual amounts of water and acetone remains at the bottom of the distillation column.

A common entrainer in this prior art process is benzene. Methods for purifying methylbutynol by distillation in the presence of benzene are disclosed in DE 1 193 496 and GB 1,023,856. Nowadays, the use of benzene is no longer considered acceptable in industrial processes for health and ecological considerations.

It is another drawback of such processes that a water/entrainer/methylbutynol ternary azeotrope containing a relatively high concentration of methylbutynol is formed. Thus either the overall yield is decreased, or additional steps for recovering methylbutynol from the azeotrope are required.

The introduction of entrainers into the distillation process has further drawbacks. Generally, entrainers render the overall process more complicated. Entrainers are found in the product and specific conditions and additional process steps have to be selected to keep the concentration of the entrainer in the methylbutynol product as low as possible. Further, the entrainer increases the total amount of the overall feed composition. Thus, the overall distillation process, which is carried out at about 100 ° C., requires more energy for evaporation and condensation of the components. Further energy and additional process steps are required for recycling the entrainer, i. e. separating it from water and methylbutynol. The use of an entrainer thus increases overall waste, emissions and complexity of the process, especially when carried out as a continuous process.

Problem Underlying the Invention

The problem underlying the invention is to provide an improved process for the purification of methylbutynol, which overcomes the above-mentioned drawbacks. The process shall be relatively simple, cost- and energy-efficient. Specifically, a process shall be provided to obtain methylbutynol from a crude reaction product comprising acetone and water. The obtainable methylbutynol product shall contain very low amounts of water, acetone and other side-products. The use of environmentally harmful substances, such as benzene or other aromatic compounds, shall be avoided.

It is a specific problem underlying the invention to provide a process which avoids the introduction of an entrainer. The process shall be applicable as a continuous process and in large industrial scale for the purification of large amounts of methylbutynol.

DETAILED DESCRIPTION OF THE INVENTION

Subject of the invention is a process for the production of methylbutynol, wherein the process comprises at least one pervaporation step. Preferably, the process comprises the steps of providing a feed composition comprising methylbutynol and water, removing a fraction of the feed composition, said fraction having a higher water content than the feed composition, and subjecting said fraction to pervaporation, thereby reducing its water content.

In a preferred embodiment, the process comprises the steps of:
(a) providing a feed composition comprising methylbutynol and water,
(b) subjecting the feed composition to distillation in a distillation device,
(c) removing a sidestream from the distillation device, the sidestream having a higher water content than the feed composition, and
(d) subjecting said sidestream to pervaporation, thereby reducing the water content of the sidestream.

The inventive method is a method for the production of methylbutynol. As used herein, the term "production" refers to any process in which a methylbutynol product is obtained wherein the methylbutynol is enriched, compared to the content in the feed composition. Thus, the process of the invention is also a process for purifying methylbutynol and/or for concentrating a composition comprising methylbutynol. Since the inventive method efficiently separates methylbutynol from water, it is also a process for dewatering methylbutynol or dewatering a composition comprising methylbutynol. The term "production" includes, but is not limited to, organic synthesis. The overall inventive process thus may comprise, but does not necessarily comprise, a step in which methylbutynol is synthesized by means of organic synthesis.

The feed composition provided in step (a) is a mixture which is fed into the distillation device of step (b). The mixture comprises the desired product methylbutynol. Further, it comprises water. In principle, the feed composition may be any composition comprising substantial amounts of methylbutynol and water. However, the method of the invention is especially applicable for producing methylbutynol from compositions comprising water as well as at least one further compound, the boiling point of which is significantly lower than 100° C. In a highly preferred embodiment, the feed composition comprises methylbutynol, water and acetone.

In a preferred embodiment of the invention, the feed composition is a crude reaction product of acetone and acetylene, or derived from such a crude reaction product. The crude reaction product of this reaction usually comprises methylbutynol, water, acetone, and ammonia. The reaction of acetone with acetylene is carried out in the presence of catalysts and solvents. Further, it is usually carried out in a basic environment, mediated by ammonia or carbonates. Thus, the crude reaction product which may be used as the feed composition in the inventive method, may comprise such solvents, catalysts, bases, and/or further additives, as well as by-products.

The feed composition provided in step (a) may be derived from such a crude reaction product. For example, the crude reaction product provided in step (a) of the inventive process may have been subjected to a preceding purification step or modification step. In a preceding purification, low or high boiling components may be removed, for example by evaporation, distillation, or sieving. In a preceding modification step, the base, such as ammonia or carbonates, may have been neutralized.

In a preferred embodiment, the feed composition is evaporated and fed into the distillation device in the gaseous state. In this embodiment, the evaporation device (evaporator) can be controlled such that methylbutynol, water, and low-boiling substances, such as acetone and ammonia, are evaporated, whereas high-boiling components, such as salts and resins, remain in the evaporator. This is highly advantageous, because in the distillation device, methylbutynol remains at the bottom of the column and thus is not separated from high-boiling components. Preferably, the evaporator is a film evaporator.

In another embodiment, before step (a) of the inventive process, the crude reaction product was subjected to prior distillation, in which low-boiling compounds, such as acetone and/or ammonia, were removed, or at least partially removed.

In preferred embodiments of the invention, the feed composition provided in step (a) comprises at least 50%, preferably at least 80% or at least 90% (w/w) methylbutynol. The water content is preferably at least 0.1%, more preferably at least 0.2%, at least 0.5%, or at least 1% (w/w). The acetone content is preferably at least 0.1%, more preferably at least 0.2%, at least 0.5%, or at least 1% (w/w). In the following, all percentages refer to weight-% (w/w), unless indicated otherwise.

In preferred embodiments of the invention, the feed composition comprises 50 to 99.5% (w/w) methylbutynol and 0.1 to 25% (w/w) water, more preferably 75 to 99% (w/w) methylbutynol and 0.2 to 10% (w/w) water, most preferably 80 to 98% (w/w) methylbutynol and 0.5 to 5% (w/w) water. Preferably, the ammonia content is between 0 and 10%, or between 0.2 and 7.5% (w/w), or between 0.5 and 5% (w/w).

In a preferred embodiment of the invention, the feed composition comprises
(i) 50 to 99.5%, preferably 75 to 99% (w/w), methylbutynol,
(ii) 0.1 to 25%, preferably 0.2 to 10% (w/w), water,
(iii) 0.1 to 25%, preferably 0.2 to 10% (w/w), acetone, and
(iv) 0 to 10%, preferably 0.2 to 7.5% (w/w), ammonia.

The distillation is carried out in a distillation device. The distillation device is usually a distillation column, especially a rectification column. At the head of the column, a distillate is collected. The distillate is enriched in low-boiling components liquid at room temperature and having a boiling point below that of water, such as acetone. The temperature at the head of the column is below the temperature in the lower part of the column.

Preferably, the head of the column comprises a condenser. Preferably, the temperature of the condenser is adjusted for obtaining a distillate with a desired composition. For example, the temperature of the condenser may be between 0° C. and 50° C., preferably room temperature (i.e., about 20° C.). The temperature may be controlled by a cooling water circuit. The temperature at the head of the column should be in the range of the condensation temperature of the low boiling components. For recovery of acetone, a temperature around 56° C., for example between 30° C. and 75° C., especially between 45° C. and 70° C., is preferred. Preferably, ammonia, which has a boiling point significantly below that of acetone, is not condensed and removed from the top of the column in gaseous form.

In a preferred embodiment of the invention, the distillate, in comparison to the feed composition, is enriched in acetone and/or ammonia. In preferred embodiments, the distillate comprises more than 50%, more preferably more than 80% (w/w) acetone. If present in the feed composition, the distillate may comprise ammonia, for example up to 15%, but preferably below 2% or below 1% (w/w) of the distillate. Preferably, most of the ammonia at the top of the column should not be condensed and not become part of the distillate. Instead, it should pass the condenser at the head of the column and leave the column in gaseous form. Preferably, the methylbutynol content of the distillate is low, for example below 5%, preferably below 2% (w/w). Preferably, the distillate comprises between 85 and 99% acetone, between 0.5 and 8% water, between 0.2 and 5% methylbutynol, and below 2% (w/w) ammonia.

It is preferred that a continuous reflux of acetone within the column is provided. Reflowing acetone supports the condensation of methylbutynol and thereby prevents methylbutynol from reaching the head of the column. In a preferred embodiment, at least a portion of the distillate is removed from the column and the process. This is advantageous in order to reduce the amount of acetone in the overall process.

Gas, which passed the condenser at the head of the column and leaves the column, usually comprises ammonia. In a preferred embodiment, it passes another external condenser for removing residual acetone and methylbutynol. The external condenser may comprise a cooling trap. Preferably, the gas passing the external condenser mostly comprises ammonia, which may be recovered with appropriate additional devices.

At the bottom of the column, a liquid distillation residue is accumulated. The distillation residue comprises high-boiling components of the feed composition. Thus the distillation residue is enriched in methylbutynol, compared to the feed composition. In a preferred embodiment of the invention, the distillation residue comprises more than 99.5% (w/w) methylbutynol and less than 0.1%, preferably less than 0.03% (w/w), water. Preferably, the temperature at the bottom of the column is slightly above 100° C., in order to ensure evaporation of water and low boiling components. For example, the temperature may be between about 100 and 110° C., preferably between 102 and 107° C.

The methylbutynol product can be collected and removed from the bottom of the distillation column. Optionally, it may be subjected to further subsequent purification steps. For example, the product may be subjected to another distillation in an additional distillation device, in which it is depleted further from low-boiling and/or high-boiling components.

In the inventive process, a water-enriched sidestream is removed from the distillation device. In other words, the water content of the sidestream is higher than the water content of the feed composition. Overall, the temperature and conditions in the distillation device should be controlled, such that low-boiling components, especially acetone, are condensed in the distillate, whereas a fraction comprising mostly methylbutynol and water is removed with the sidestream. After removal from the distillation device, the sidestream is subjected to pervaporation.

In a distillation column, a distillate is obtained at the head of the column, whereas a distillation residue is obtained at the bottom of the column. Sidestream products are obtainable at any desired position beneath the head of the column and above the bottom of the column. According to the invention, the sidestream may be removed at any position between the head and the bottom of the column, provided that it is water-enriched. Typically, a sidestream fraction is collected in appropriate means in a distillation device, such as trays, and led to an outlet at the desired position (height). Distillation devices, from which sidestreams are obtained, are known in the art.

Preferably, the sidestream consists mostly of methylbutynol and water. Preferably, the sidestream comprises more than 90% (w/w), more preferably more than 95% (w/w) methylbutynol, and water. In a preferred embodiment of the invention, the water-enriched sidestream in step (c) comprises 50 to 95% (w/w) methylbutynol and 10 to 40% (w/w) water, more preferably between 70 and 90% (w/w) methylbutynol and 15 to 30% (w/w) water. The sidestream may comprise an azeotrope of methylbutynol and water. At about 91° C., water and methylbutynol form an azeotrope consisting of about 70.5 to 72.5% (w/w) methylbutynol and 27.5 to 29.5% (w/w) water. However, it is not necessary to achieve perfect azeotropic conditions in the sidestream. Water depletion can be carried out efficiently, when any sidestream having a high water and methylbutynol content is removed from the distillation device and subjected to pervaporation. The sidestream may comprise low amounts of acetone and ammonia, for example up to 5% (w/w) acetone and up to 1% (w/w) ammonia.

The sidestream is subjected to pervaporation. Pervaporation is a method for the separation of mixtures of liquids by partial vaporization through a membrane. The membrane acts as a selective barrier between the two phases, the liquid phase feed and the vapor phase permeate. At least one component of the liquid feed is transferred through the membrane by vaporization. The high molecular weight components of the feed remain in the retentate. Typically, the upstream side of the membrane is at ambient pressure and the downstream side (permeate side) is under vacuum or reduced pressure. Thereby, the selective component is evaporated after permeation through the membrane. It thus cannot form a liquid film, which might block the membrane. The difference in the partial pressures of the components on the two sides is the driving force for the separation.

Pervaporation has been used in the art for separating liquid mixtures, for example for removing solvents from liquid compositions (Fontalvo Alzate, J. (2006), "Design and performance of two-phase flow pervaporation and hybrid distillation process", TU Eindhoven, Netherlands, ISBN 978-90-386-3007-6). Pervaporation is also used for carrying out and actively supporting equilibrium reactions (Waldburger, R. et al. (1994), Kombination von Veresterung und Pervaporation in einem kontinuierlichen "Membranreaktor", Chem. Ing.-Tech. 66, p. 850-54, VCH Weinheim, DE).

According to the invention, at least one pervaporation device is used, which is capable of separating water from methylbutynol. Membranes for the removal of water from organic compounds are known in the art. In a preferred embodiment of the invention, the pervaporation is carried out with a hydrophilic membrane, preferably a polyvinyl alcohol membrane or a polyimide membrane. Alternatively, the membrane may be a ceramic membrane, for example based on zeolite A. Ceramic membranes for pervaporation comprise nanoporous layers on macroporous supports. The pores must be large enough to let water molecules pass through and small enough to retain methylbutynol. The surfaces may be modified by specific coatings or treatments. Such membranes have been used for water removal from organic reaction mixtures (Waldburger, R. et al. (1994), see above) and are available from Folex, Switzerland (formerly CM-Celfa Membranes, Switzerland). Further applicable membranes are available from Sulzer Chemtech Ltd., Switzerland, and were available from GFT, Gesellschaft für Trenntechnik, Germany.

In the pervaporation step, the water content of the sidestream is reduced. Preferably, the water content of the retentate is reduced to less than 50%, less than 20%, or less than 10% of the water content of the sidestream. Preferably, the retentate of the pervaporation comprises less than 10%, preferably less than 6% or more preferably less than 3% (w/w) water. Preferably, the water content in the retentate is between 0.1% and 10% or between 1% and 8% (w/w). Typically, pervaporation of a sidestream comprising about 15 to 25% (w/w) water may reduce the water content to about 0.1 to 10% (w/w). The water content in the retentate may be reduced further, for example by using several pervaporation devices or membranes in series. The water content may also be reduced further by reintroducing the pervaporation retentate into the pervaporation feed. For example, the water content could be reduced further by combining two, three or more pervaporation devices and/or membranes in series and/or by passing the retentate two, three or more times through the pervaporation device. When reducing the water content to such levels and recycling the retentate, water can be removed efficiently from the overall process whilst reducing the loss of methylbutynol to a minimum.

The permeate, which mostly comprises water, is removed from the overall process. It can be discarded or recycled, for example to recover residual methylbutynol or acetone. Depending on the membrane and pervaporation conditions selected, the permeate may comprise methylbutynol, for example between 1 and 15% (w/w). In a specific embodiment, the methylbutynol is separated from the permeate and reintroduced into the distillation device.

The at least partially dewatered retentate comprises a high ratio of methylbutynol. In a preferred embodiment of the invention, the retentate of the pervaporation is reintroduced into the distillation device, preferably continuously. For example, it may be combined with feed composition and re-fed into the distillation column. Thus, the overall loss of methylbutynol is minimized, whereas water is efficiently removed from the overall process. When removing water continuously by pervaporation, the water content in the methylbutynol product can be reduced significantly.

Preferably, the pervaporation is carried out with a liquid sidestream. The temperature of the sidestream at the location where it is withdrawn from the column may be between 75 and 98° C., preferably between 85 and 95° C. Before entering the pervaporation device, the temperature of the sidestream may be adjusted to a temperature suitable for pervaporation, for example between 80 and 100° C.

In another embodiment of the invention, the sidestream is gaseous. The pervaporation could then be carried out with the gaseous sidestream. This would be energetically advantageous, but requires the use of membranes stable at the boiling point of the methylbutynol of about 104° C.

In a preferred embodiment of the invention, the process comprises the steps of
(a) providing a feed composition comprising methylbutynol, acetone and water,
(b) subjecting the feed composition to distillation in a rectification column,
(c) removing a sidestream from the distillation column, the sidestream having a higher water content than the feed composition and comprising 50 to 95% (w/w) methylbutynol and 10 to 40% (w/w) water,
(d) subjecting said sidestream to pervaporation, thereby reducing the water content, and
(e) reintroducing the retentate of the pervaporation obtained in step (d) into the distillation column,
wherein acetone and low-boiling compounds are removed with condensed distillate, and purified methylbutynol is removed with the distillation residue.

In a preferred embodiment of the invention, the process is a continuous process. In a continuous process, the feed composition is continuously introduced into the distillation device. Further, the sidestream is continuously removed and subjected to pervaporation. The pervaporation retentate, which is enriched in methylbutynol, is re-fed into the process. Overall, the feed composition is continuously dewatered. Methylbutynol is collected at the bottom of the device, being depleted of water as well as low-boiling components, especially acetone and ammonia. Preferably, the continuous process is adjusted to equilibrium conditions. In other words, the reaction conditions, such as product concentrations, temperatures, pressures etc., in the distillation device are approximately stable. In such a process, purified methylbutynol can be withdrawn continuously from the bottom of a column. Usually, equilibrium conditions can be obtained after an industrial process is run under controlled conditions for at least several hours or days.

The inventive process can be carried out with known distillation devices. Preferably, the distillation device is a distillation column, especially a rectification column. Rectification is a type of counter-current distillation, in which two fluid streams are moving in opposite directions. As the first fluid stream, a vapor stream moves upwards inside the column and is condensed at the top of the column. At least part of the condensate flows back into the column and moves downwards as the second fluid stream, which is a countercurrent liquid stream. A rectification column usually comprises means for increasing the contact area between the two streams, such as trays, especially bubble trays. The means may also be sieves, fillings or structured packages. Rectification columns are well-known in the art. The distillation device may also comprise multiple distillation columns, for example two or three distillation columns. However, it was found that a single column, combined with the pervaporation step, is sufficient to obtain a high yield of methylbutynol.

Preferably, the distillation column is a sidestream column. Sidestream columns are distillation columns, usually rectification columns, for obtaining at least three fractions from a feed composition, which are distillate, distillation residue and sidestream. The design and operation of sidestream distillation columns is known in the art and described, for example, in Glinos and Malone (1985), Ind. Eng. Chem. Process Des. Dev., 822-828.

In another preferred embodiment of the invention, the distillation device is a dividing wall column. Usually, a dividing wall column is a rectification column. In addition to the horizontal compartments, such as trays, a dividing wall column comprises a vertical wall within the column, which separates two compartments from each other. The feed is introduced on one side of the wall, whereas a sidestream accumulates and can be withdrawn on the opposite side of the wall.

In a preferred embodiment of the invention, the distillation, in which the sidestream is removed, is not carried out in the presence of an entrainer. In the state of the art, methylbutynol is usually purified from aqueous compositions by distillation in the presence of entrainers, such as benzene, which form an azeotrope with water. As noted above, the use of entrainers is disadvantageous for a number of reasons. For example, entrainers increase the cost and energy consumption of such processes and introduce another undesired component, which finally has to be removed from the product. Further, the water/entrainer azeotrope usually comprises a relatively high amount of methylbutynol, and thus the yield is decreased or additional separation steps have to be applied. In the inventive process, which uses pervaporation for removing water, methylbutynol can be efficiently purified and dewatered without addition of an entrainer. Specifically, when combining pervaporation with a distillation as outlined above, water and other components can be removed nearly quantitatively in a relatively simple process without an entrainer. This renders the overall process effective, cost- and energy-efficient.

In specific preferred embodiments, no aromatic entrainer is added prior to or during the distillation, during which the sidestream is removed. It is also not necessary to include another process step, in which methylbutynol is further purified, or pre-purified, in the presence of an entrainer. However, the inventive process may be carried out in the presence of an entrainer, for example if considered necessary for increasing product purity. When adding an entrainer in the distillation with the sidestream removal, it is preferred to use only a little amount, for example below 2% (w/w) or below 1% (w/w) of the feed composition.

In a preferred embodiment of the invention, the feed composition is fed into the distillation column in the gaseous state. The feed composition can be converted into a gas with an evaporator. Usually, an evaporator produces a gaseous phase under reduced pressure or normal pressure, for example between 1 kPa (10 mbar) and 100 kPa (1 bar) absolute. The residence time of the feed composition in the evaporator is preferably as low as possible. A low residence time can be achieved in a film evaporator, for example.

In another preferred embodiment, a natural or forced circulation evaporator is positioned at the bottom of the column. The distillation residue is circulated in the circulation evaporator in order to improve separation of water, acetone and other volatile components from the distillation residue.

Preferably, the methylbutynol produced according to the inventive process comprises more than 99% (w/w) methylbutynol, more preferably more than 99.5% or more than 99.7% (w/w) methylbutynol. Preferably, it comprises less than 0.1%, preferably less than 0.05% or less than 0.03% (w/w) water.

Subject of the invention is also the use of pervaporation and/or a pervaporation membrane for removing water from methylbutynol, or in a method for purifying methylbutynol.

Subject of the invention is also a device for carrying out a process of any of the preceding claims, comprising a distillation column and means for pervaporation, the device comprising methylbutynol.

Figure 1:
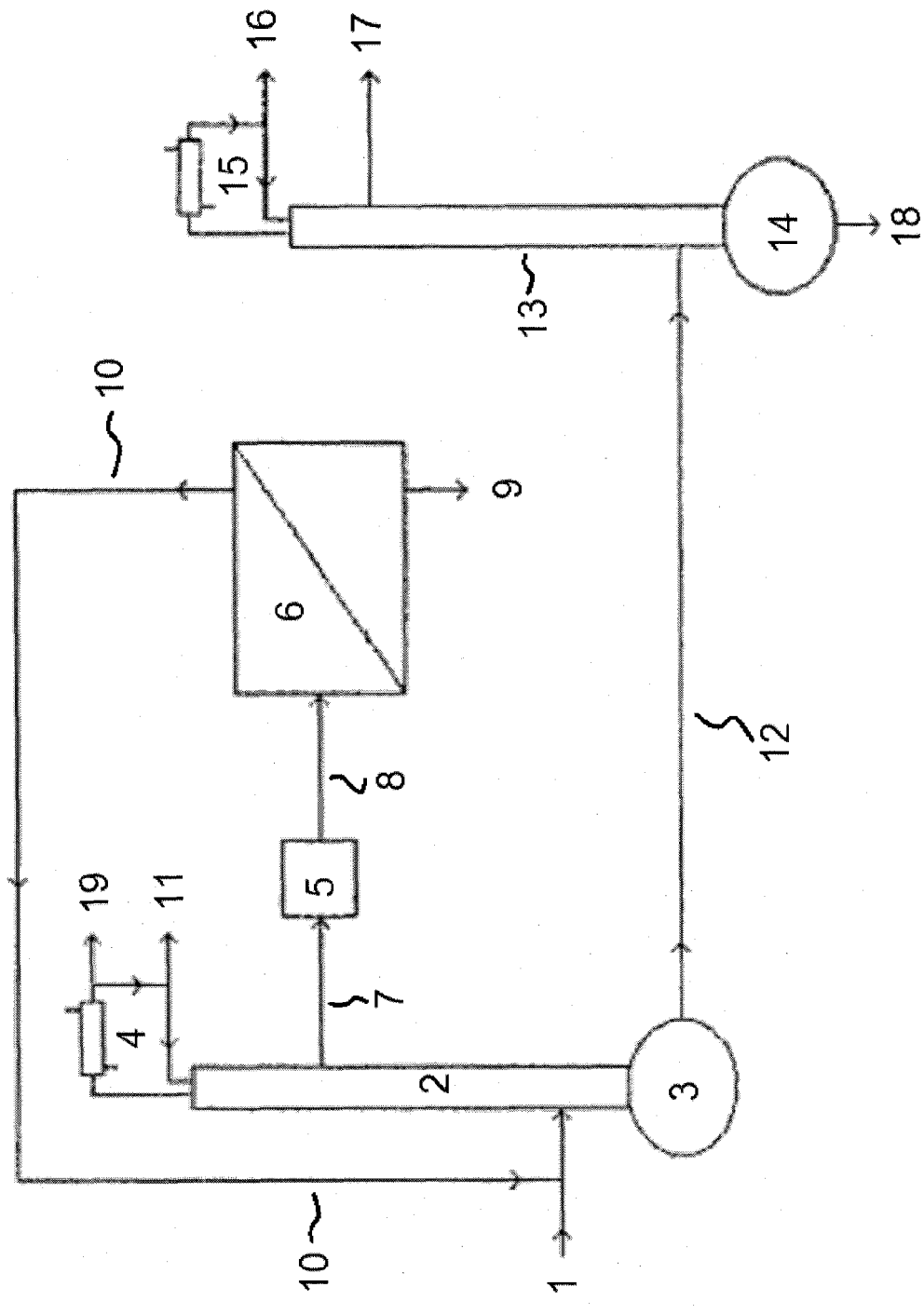
FIG. 1 schematically shows an exemplified process design for the production of methylbutynol according to the invention.

A feed composition 1 comprising methylbutynol and water is fed into a distillation device. The distillation device is a column 2 comprising a bottom 3 and head 4. In the distillation process, low-boiling components which are liquid at room temperature, especially acetone, are condensed in a condenser at the head of the column and removed through outlet 11. Ammonia, which is not condensed, mostly passes the condenser and is removed in gaseous form through outlet 19. Methylbutynol is collected in the distillation residue at the bottom 3. A sidestream is removed from the column through conduit 7. The sidestream may be collected in a tank 5. It is transferred into a pervaporation device 6 through conduit 8. The water is enriched in permeate and removed through outlet 9. The water may be discarded or recycled. The retentate, which is dewatered and also enriched in methylbutynol, is transferred through connections 10 and re-introduced into the feed composition 1. Thereby, water is removed from the overall process. At the bottom of the column, methylbutynol, i. e. a composition comprising a high ratio of methylbutynol, is removed through connection 12. According to the invention, the methylbutynol removed through connection 12 has a high purity and low water content, as well as a low content of low-boiling components.

Optionally, the methylbutynol may be subjected to subsequent purification steps. For example, the methylbutynol product may be distilled in a subsequent second distillation column 13. In column 13, high-molecular weight components, such as undesired side-products, are maintained at the bottom of the column, whereas methylbutynol is isolated in a sidestream 17. At the top of the column, a methylbutynol/water azeotrope could be isolated through connection 16, after condensation in a condenser 15. Thus, the water (and acetone) content could be decreased further. In a specific embodiment, the azeotrope 16 could be re-introduced into the pervaporation device 6 or into the first distillation column 2 at a height between stream 1 and stream 7.

Figure 2:
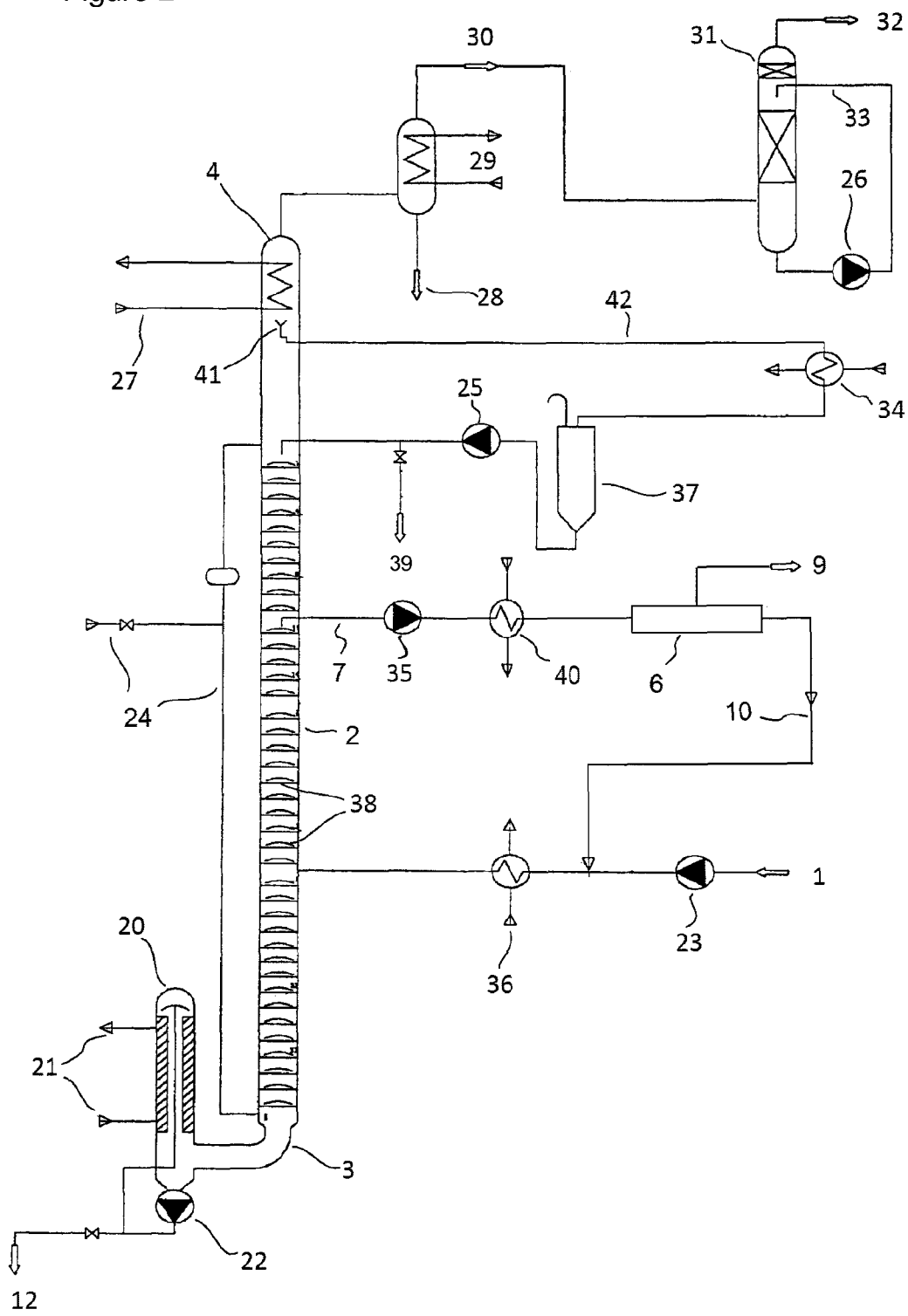

FIG. 2 schematically shows an exemplified distillation device for the production of methylbutynol according to the invention.

A feed composition 1 comprising methylbutynol, water, acetone and ammonia is fed by pump 23 into a distillation device 2, which is a rectification column comprising bubble cap trays 38. The feed is heated by heater 36. The liquid distillation residue accumulates at the bottom 3 of the column 2. A falling film evaporator 20 heated by oil circulation 21 is located at the bottom 3 of the column. The product is withdrawn through connections 12 via pump 22. A sidestream 7 consisting mostly of water and methylbutynol is withdrawn from column 2 by pump 35 and cooled by cooler 40. The sidestream is subjected to pervaporation in pervaporation device 6 and thereby depleted of water. The water is enriched in the permeate and removed through outlet 9. The water may be discarded or recycled. The retentate, which is dewatered and also enriched in methylbutynol, can be re-introduced into the feed stream through connections 10. The retentate, which is enriched in methylbutynol, is thus reintroduced into column 2. Thereby, water is removed from the overall process.

The temperature of column 2 is controlled by circuit 24. A partial condenser 27 is located at the head 4 of column 2, from which liquid distillate can reflow into the column. Distillate is removed from the column by fluid separator 41 positioned underneath the partial condenser 27 through connections 42, passes distillate cooler 34 and is collected in container 37. The distillate is enriched in acetone and can be refluxed and partially removed from the process through outlet 39 by pump 25. At the head 4 of the column, gas which is not condensed in partial condenser 27 is transferred to an external condenser 29, which is a brine condenser. Condensed liquid, which is enriched in acetone, accumulates in cooling trap 28, from which it can be discarded or recycled. The gas stream which passes external condenser 29 is enriched in ammonia and transferred through connections 30 by pump 26 into ammonia absorption device 31 comprising a temperature control circuit 33. Exhaust gas is removed through outlet 32.

The inventive process solves the problems underlying the invention. The invention provides a relatively simple, cost- and energy-efficient process for the production of a highly pure methylbutynol.

No addition of an entrainer is necessary, and thus the drawbacks of entrainers can be avoided. The product does not comprise entrainer impurities. Environmental problems associated with aromatic entrainers are avoided. The overall process can be handled and adjusted more easily and conveniently, because no formation of ternary entrainer azeotropes with water and methylbutynol has to be taken into account. Therefore, the loss of methylbutynol is lower and the overall thermodynamic separation problem is less complicated in the inventive process.

The energy consumed in the inventive process is basically equal to the evaporation energy of the feed composition and condensation energy of the permeate. In the distillation column, into which the feed composition is introduced, the methylbutynol is not distilled and condensed, but enriched in the distillation residue. In contrast, in state of the art entrainer process, additional energy is used for evaporation and condensation of the entrainer. It was calculated that the overall process of the invention requires about 10 to 40% less energy, compared to a conventional entrainer process.

EXAMPLES

Example 1

Simulation

The process was simulated in industrial scale with process simulation software (trademark ChemCAD 6; Chemstation, US). The simulation comprised three consecutive columns. Process conditions and results are summarized in Table 1. The simulation yielded information about optimized conditions and compositions of process fractions for carrying out the process. Moreover, it shows that a sidestream composition is obtained enriched in methylbutynol and water in concentrations suitable for water depletion by pervaporation.

Examples 2 and 3

Laboratory Scale

The process was carried out at laboratory scale. Process conditions and results are summarized in Table 1. The distillation device consisted of three consecutive columns arranged on top of each other. The distillation residue was collected in a flask. At the head of the upper column, liquid was condensed with a backflow condenser and condensate was removed after passing a reflow partitioner. A sidestream was collected at a position below the upper column and above the middle column. At the bottom of the column, methylbutynol is enriched in concentrated form (99.6/99.7% w/w). Acetone is accumulated in the condenser and the distillate, whereas the concentration of methylbutynol is 0.15/0.2% (w/w) in the condenser and 11.5% (w/w) in the distillate. In Example 2, the sidestream comprised 65.9% (w/w) methylbutynol and 21.6% (w/w) water. In Example 3, the sidestream comprised 78.4% (w/w) methylbutynol and 18.8% water (w/w). The sidestream is thus suitable for water depletion by pervaporation. Overall, the results show that methylbutynol is obtained in highly concentrated form, the loss of methylbutynol is low and water can be removed efficiently by pervaporation.

Example 4

Pilot Scale

The process was carried out at a pilot scale. Process conditions and results are summarized in Table 1. The rectification column comprised 30 bubble cap trays having a diameter of 50 mm. The feed was introduced in gaseous form above tray 20. The sidestream was removed at the position of tray 8. The partial condenser had a temperature of 20° C. and the external condenser had a temperature of −10° C. At the bottom of the column, methylbutynol is obtained in concentrated form (99.7% w/w). Acetone is enriched in the condenser and the distillate, whereas the concentration of methylbutynol is 0% in the condenser and 1% (w/w) in the distillate. A sidestream enriched in methylbutynol (78.9% w/w) and water (18.8% w/w) is isolated, which is suitable for water depletion by pervaporation. Overall, the results show that methylbutynol is obtained in highly concentrated form, the loss of methylbutynol is very low and water can be removed efficiently by pervaporation.

Example 5

Pervaporation

Pervaporation was carried out with fractions enriched in methylbutynol and water as obtained in the sidestreams by processes of Examples 1 to 4. An artificial mixture of about 70% pure methylbutynol, 28% water, 1% acetone, 1% ammonia and 0.1% acetic acid (w/w) was subjected to pervaporation. Pervaporation was carried out with a device comprising a feed container with a circulation pump, a heated pervaporation cell with a membrane (CMC-E, Celfa AG, Switzerland) and a subsequent condenser. The permeation was carried out at about 90° C. and the low was adjusted to 880 g/m$^2$h over a duration of 710 hours. A water-enriched permeate was removed in gaseous form through the membranes. The retentate comprised about 91.5% methylbutynol, 6.3% water, 1.3% acetone and 0.9% ammonia. The permeate mainly comprised water with about 0.1% methylbutynol, 0.05% acetone and 1.5% ammonia. Overall, the feed could be significantly depleted of water, whereas the loss of methylbutynol with the permeate was extremely low. The water content in the retentate could be reduced further to about 2% (w/w) by reducing the flow. The methylbutynol concentration in the permeate was then raised to 2% (w/w), which is still low and acceptable. Overall, the results show that water depletion by pervaporation is highly efficient.

The operating conditions and results of Examples 1 to 4 are summarized in Table 1. The following abbreviations indicate the type of packing material used to pack the columns:
RG=Raschig rings (glass)
WS=wire spirals
BCT=bubble cap trays

TABLE 1

Conditions and results of Examples 1 to 4.

| | | Example | | | |
|---|---|---|---|---|---|
| | | 1 | 2 | 3 | 4 |
| Column 1 | Dimensions [mm] | 6 trays | 370 × 13 | 370 × 13 | 10 BCT |
| | Packing material | | WS 2 × 2 | WS 2 × 2 | 8 trays |
| Column 2 | Dimensions [mm] | 9 trays | 550 × 25 | 550 × 25 | 15 BCT |
| | Packing material | | RG 6 × 6 | RG 6 × 6 | 12 trays |
| Column 3 | Dimensions [mm] | 15 trays | 700 × 25 | 700 × 25 | 15 BCT |
| | Packing material | | RG 6 × 6 | RG 6 × 6 | 10 trays |
| Reflux ratio | | 15:1 | ∞ | 40:1 | 12:1 |
| Streams | Condenser [%] | 1.3 | 5.8 | 4.5 | 1.1 |
| | Distillate [%] | 3.5 | | 2.8 | 6.1 |
| | Sidestream [%] | 9.1 | 10.4 | 9.4 | 10.3 |
| | Feed (100%) [kg/h] | 3280 | 0.180 | 0.180 | 3.3 |
| | Product discharge (bottom) [%] | 78.8 | 83.6 | 81.1 | 79.4 |
| Temperatures [° C.] | Head [° C.] | 54 | 53 | 69 | 59 |
| | Sidestream [° C.] | 88-91 | 86.5 | 90 | 86 |
| | Feed height [° C.] | 99.5 | 97 | 99 | 98 |
| | Feed [° C.] | 98 | 92 | 92 | 116 |
| | Bottom [° C.] | 102.5 | 104.5 | 104.5 | 105 |
| MBI | Condenser [%] | 0 | 0.15 | 0.2 | 0 |
| | Distillate [%] | 0.88 | | 11.5 | 1.0 |
| | Sidestream [%] | 77.7 | 65.9 | 78.4 | 78.9 |
| | Feed [%] | 92.5 | 88.7 | 88.9 | 92.5 |
| | Bottom [%] | 99.8 | 99.6 | 99.7 | 99.7 |
| Water | Condenser [%] | 0 | 7.35 | 5.5 | 0 |
| | Distillate [%] | 2.49 | | 15.0 | 3.8 |
| | Sidestream [%] | 20.5 | 21.6 | 18.8 | 18.8 |
| | Feed [%] | 2.14 | 2.5 | 2.3 | 2.2 |
| | Bottom [%] | 0.03 | 0.03 | 0.1 | 0.02 |

TABLE 1-continued

Conditions and results of Examples 1 to 4.

|  |  | Example 1 | Example 2 | Example 3 | Example 4 |
|---|---|---|---|---|---|
| Acetone | Condenser [%] | 11.8 | 35.7 | 40.7 | 93.9 |
|  | Distillate [%] | 87.7 |  | 60.1 | 94.5 |
|  | Sidestream [%] | 1.5 | 12.1 | 2.2 | 1.8 |
|  | Feed [%] | 3.65 | 5.5 | 5.5 | 3.6 |
|  | Bottom [%] | 0.07 | 0.05 | <0.05 | 0.06 |
| Ammonia | Condenser [%] | 88.2 | 56.8 | 53.6 | 6.1 |
|  | Distillate [%] | 8.88 |  | 8.6 | 0.6 |
|  | Sidestream [%] | 0.3 | 0.3 | 0.5 | 0.4 |
|  | Feed [%] | 1.6 | 3.1 | 3.1 | 1.7 |

The invention claimed is:

1. A process for the production or purification of methylbutynol (2-methyl-3-butyn-2-ol), comprising the steps of
   (a) providing a feed composition comprising methylbutynol, water, and acetone,
   (b) subjecting the feed composition to distillation in a distillation device,
   (c) removing a sidestream from the distillation device, the sidestream having a higher water content than the feed composition, and
   (d) subjecting said sidestream to pervaporation, thereby reducing the water content.

2. The process of claim 1, wherein the feed composition is a crude reaction product of acetone and acetylene, or derived from such a crude reaction product.

3. The process of claim 1, wherein the feed composition comprises 50 to 99.5% (w/w) methylbutynol and 0.1 to 25% (w/w) water.

4. The process of claim 1, wherein the feed composition comprises
   (i) 50 to 99.5% (w/w), methylbutynol,
   (ii) 0.1 to 25% (w/w), water,
   (iii) 0.1 to 25% (w/w), acetone, and
   (iv) 0 to 10% (w/w), ammonia.

5. The process of claim 1, wherein the feed composition in step (a) comprises acetone, wherein the distillate obtained from the distillation is enriched in acetone, compared to the feed composition, and/or wherein the distillation residue is enriched in methylbutynol, compared to the feed composition.

6. The process of claim 1, wherein the distillation is carried out in the absence of an entrainer.

7. The process of claim 1, wherein the sidestream in step (c) comprises 50 to 95% (w/w) methylbutynol and 10 to 40% (w/w) water.

8. The process of claim 1, wherein the pervaporation is carried out with a polyvinyl alcohol membrane, polyimide membrane or ceramic membrane.

9. The process of claim 1, wherein the pervaporation is carried out at a temperature between 80° C. and 100° C.

10. The process of claim 1, wherein the retentate of the pervaporation is reintroduced into the distillation device.

11. The process of claim 1, wherein the distillation residue comprises more than 99.5% (w/w) methylbutynol and less than 0.1.

12. The process of claim 1, wherein the process is a continuous process.

13. The process of claim 1, wherein the feed composition comprises
   (i) 75 to 99% (w/w) methylbutynol,
   (ii) 0.2 to 10% (w/w) water,
   (iii) 0.2 to 10% (w/w), acetone,
   (iv) 0.2 to 7.5% (w/w), ammonia.

14. The process of claim 1, wherein the distillation residue comprises more than 99.5% (w/w) methylbutynol and less than 0.03%, (w/w) water.

* * * * *